United States Patent
Arnold et al.

(10) Patent No.: US 6,316,448 B1
(45) Date of Patent: Nov. 13, 2001

(54) PYRAZOLO[3,4-D][1,2,3] TROAZINES HAVING ANTICONVULSANT ACTIVITY AND PROCESS FOR THEIR PREPARATION

(76) Inventors: Thomas Arnold, Coswiger Strasse 14a, D-01445 Radebeul; Klaus Unverferth, Gerokstrasse 30, D-01307 Dresden; Hans-Joachim Lankau, Coswiger Strasse 19, D-01689 Weinböhla; Angelika Rostock, Makarenkostrasse 7, D-01445 Radebeul; Reni Bartsch, Weinbergstrasse 23, D-01458 Ottendorf-Okrilla; Thomas Kronbach, Elbstrasse 3 B, D-01445 Radebeul, all of (DE)

( * ) Notice: Subject to any disclaimer, the term of this patent is extended or adjusted under 35 U.S.C. 154(b) by 0 days.

(21) Appl. No.: 09/575,479

(22) Filed: Apr. 19, 2000

(30) Foreign Application Priority Data

May 29, 1999 (DE) .............................................. 199 24 872

(51) Int. Cl.[7] .......................... A61K 31/53; C07D 487/04
(52) U.S. Cl. ............................................. 514/243; 544/184
(58) Field of Search .............................. 544/184; 514/243

(56) References Cited

U.S. PATENT DOCUMENTS 2,925,418 * 2/1960 Draey et al. ......................... 544/184

* cited by examiner

*Primary Examiner*—Richard L. Raymond

(57) ABSTRACT

The invention relates to 3,6-dihydropyrazolo[3,4-d][1,2,3] triazin-4-ones and their tautomers, which contain a benzyl radical in the 6 position, processes for their preparation and their use as medicaments, in particular for the treatment of epilepsy of various forms.

8 Claims, No Drawings

PYRAZOLO[3,4-D][1,2,3] TROAZINES HAVING ANTICONVULSANT ACTIVITY AND PROCESS FOR THEIR PREPARATION

The invention relates to pyrazolo[3,4-d][1,2,3]triazin-4-ones and their tautomers, which contain a benzyl radical in the 6 position, processes for their preparation and their use as medicaments, in particular for the treatment of epilepsy of various forms.

Unsubstituted pyrazolo[3,4-d][1,2,3]triazin-4-onewas describedin 1968 [Cheng et al., J. Pharm. Sci. 1968, 57, 1044]. Up to now, only 7-substituted triazine derivatives have been obtained by diazotization of substituted aminopyrazolecarboxamides [Gatta, Franco, Luciani, Maria, Palazzo, J. Heterocycl. Chem. 1989, 26, 613].

Isomeric compounds such as 7-(2-fluorobenzyl)-3,6-dihydropyrazolo[3,4-d][1,2,3]triazin-4-one and 7-(2-fluorobenzyl)-7H-imidazo[4,5-d][1,2,3]triazin-4-one were described in 1995 [J. L. Kelley, D. C. Wilson, V. L. Styles, F. E. Soroko, B. R. Cooper, J. Heterocyclic Chem. 1995, 32, 1417].

3,6-Dihydropyrazolo[3,4-d][1,2,3]triazin-4-ones and tautomers which have a (substituted) benzyl radical in the 6 position have hitherto not been described in the literature.

Epilepsy is a behavioral change in the form of convulsions. The cause is short-term, extremely strong neuronal discharges of the brain. Altogether, about 5% of all people suffer an epileptic attack in their life; 1% suffer from epilepsy.

Fundamentally, two factors are to be considered for the genesis of convulsions, pathological discharges in groups of nerve cells and/or absent stimulus limitation which makes possible a spread of the pathological stimulation, that is there is an increased instability of the cell membrane potential with a tendency for spontaneous electrical discharges.

Only approximately 60–80% of the patients presently become attack-free under medicinal treatment. Certain forms of epilepsy, however, can still not be treated adequately.

In addition, undesired side effects, such as neurotoxicity and idiosyncrasy, can occur through the administration of anticonvulsants found on the market.

The invention is therefore based on the object of making available compounds having favorable pharmacological properties, which can be employed as medicaments, in particular for the treatment of epilepsy.

According to the present invention, these novel compounds are 6-ar(alkyl)-3,6-dihydropyrazolo[3,4-d][1,2,3]triazin-4-ones of the general formula 1

Formula 1

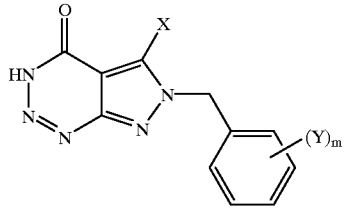

or their tautomers, where x=hydrogen or C1–C4-alkyl;

Y=hydrogen, halogen, C1–C4alkyl, C1–C4-alkoxy, trifluoromethyl or trifluoromethoxy and m=1 or 2.

Examples of compounds of the general formula 1 which may be mentioned are:

6-(2-fluorobenzyl)-3,6-dihydropyrazolo[3,4-d][1,2,3]triazin-4-one 6-(2-chlorobenzyl)-3,6-dihydropyrazolo[3,4-d][1,2,3]triazin-4-one 6-(2-trifluoromethylbenzyl)-3,6-dihydropyrazolo[3,4-d][1,2,3]triazin-4-one 6-(2-methylbenzyl)-3,6-dihydropyrazolo[3,4-d][1,2,3]triazin-4-one 6-(3-chlorobenzyl)-3,6-dihydropyrazolo[3,4-d][1,2,3]triazin-4-one 6-(3-trifluoromethylbenzyl)-3,6-dihydropyrazolo[3,4-d][1,2,3]triazin-4-one 6-(4-fluorobenzyl)-3,6-dihydropyrazolo[3,4-d][1,2,3]triazin-4-one 6-(4-chlorobenzyl)-3,6-dihydropyrazolo[3,4-d][1,2,3]triazin-4-one 6-(2-chloro-6-fluorobenzyl)-3,6-dihydropyrazolo[3,4-d][1,2,3]triazin-4one 6-(2-chlorobenzyl)-5-methyl-3,6dihydropyrazolo[3,4-d][1,2,3]triazin-4one 6-(2-chloro-4-fluorobenzyl)-5-methyl-3,6-dihydropyrazolo[3,4-d][1,2,3]triazin-4-one 6-benzyl-3,6-dihydropyrazolo[3,4-d][1,2,3]triazin-4-one The process for the preparation of compounds of the formula 1 and their tautomers is based on the cyclization of 3-aminopyrazole-4-carboxamides of the general formula 2 formula 2

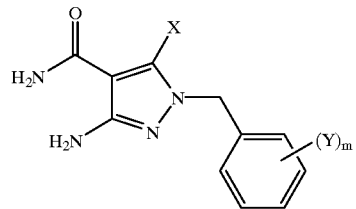

in which

X=hydrogen or C1–C4-alkyl;

Y=halogen, C1–C4-alkyl, C1–C4-alkoxy, trifluoromethyl or trifluoromethoxy and m=1 or 2, with sodium nitrite in aqueous hydrochloric acid or with alkyl nitrites in ethanolic hydrochloric acid.

The process for the preparation of compounds of the formula 2 starts from 3-aminopyrazole-4-carboxylic acid derivatives [R. K. Robins; J. Am. Chem. Soc 1956, 784; P. Schmidt, J. Druey Helv. Chim. Acta 1956, 39, 986].

The compounds of the formula 2 are obtained by alkylation under phase-transfer conditions with a suitably substituted benzyl halide [S. Senda, K. Hirota, G.-N. Yang, Chem. Pharm. Bull 1972, 20(2), 3919 .

Alternatively, 3-aminopyrazole-4-carbonitriles can be alkylated with a suitably substituted benzyl halide under phase-transfer conditions. Compounds of the formula 2 are obtained by acidic hydrolysis of the nitrile, preferably in conc. sulfuric acid [R. K. Robins; J. Am. Chem. Soc 1956, 784].

The compounds according to the invention have strong anticonvulsive actions, which are described in greater detail below.

Anticonvulsive activity

The compounds according to the invention were tested in vivo for their anticonvulsive action (Table 1) in mice (i.p. administration) or rats (p.o. administration) according to the internationally customary standard (Pharmac. Weekblad, Sc. Ed. 14, 132 (1992) and Antiepileptic Drugs, Third. Ed., Raven Press, New York 1989).

Analogous results were obtained for the oral action. For example, for compound 2 (6-(2-chlorobenzyl)-3,6-dihydropyrazolo[3,4-d][1,2,3]triazin-4-one) in the rat in maximal electroshock the ED50 (p.o.) was determined to be 3 mg/kg and for the neurotoxicity the NT50 was determined to be >250 mg/kg.

TABLE 1

Anticonvulsive action of selected pyrazolo[3,4-d]triazines of the formula 1

| Compound[1] | Log P[2] | Test[3] | Dose[4] | Action[5] |
|---|---|---|---|---|
| 1 | n | MES | 30 | 100 |
|   |   | PTZ | 100 | 66 |
| 2 | 0.82 | MES | 30 | 100 |
|   |   | PTZ | 30 | 60 |
| 3 | 1.74 | MES | 30 | 33 |
|   |   | PTZ | 100 | 100 |
| 4 | 0.74 | MES | 30 | 100 |
|   |   | PTZ | 300 | 100 |
| 5 | 1.83 | MES | 100 | 100 |
|   |   | PTZ | 300 | 0 |
| 6 | 2.02 | MES | 100 | 66 |
|   |   | PTZ | 100 | 20 |
| 7 | 1.28 | MES | 100 | 66 |
|   |   | PTZ | 300 | 100 |
| 8 | 1.88 | MES | 300 | 100 |
|   |   | PTZ | 300 | 100 |
| 9 | 1.38 | MES | 10 | 20 |
|   |   | PTZ | 100 | 100 |
| 10 | n | MES | 100 | 66 |
|   |   | PTZ | 300 | 0 |
| 11 | n | MES | 100 | 66 |
|   |   | PTZ | 100 | 33 |
| 12 | n | MES | 100 | 66 |
|   |   | PTZ | 100 | 0 |
| Comparison substances |   | MES | 100 | 100 |
| Carbamazepine |   | PTZ | 100 | 0 |
|   |   | MES | 100 | 0 |
| Valproate |   | PTZ | 100 | 30 |

Notes for Table 1:
[1] Numbering of the compounds corresponding to the examples in Table 2
[2] Octanol/water partition coefficient, n = not measured
[3] Mouse i.p.: MES = maximal electroshock, PTZ = s.c. pentetrazol
[4] in mg/kg
[5] in % of the protected animals It can be seen from Table 1 that the compounds according to the invention have strong anticonvulsant activity and exhibit no or only a low neurotoxicity.

The compounds of the formula 1 according to the invention are suitable for the production of pharmaceutical compositions. These pharmaceutical compositions contain at least one of the compounds of the general formula 1 according to the invention and, if appropriate, customary pharmaceutical vehicles and/or excipients. The pharmaceutical preparations can be administered, for example, parenterally (intravenously, intramuscularly subcutaneously) or orally.

The administration forms can be prepared by processes which are generally known and customary in pharmaceutical practice.

The following examples serve to illustrate the invention further without restricting it.

General procedure for the preparation of the compounds of the formula 1 and their tautomers as in Table 2, Examples 1–12

30 mmol of compound of the formula 2 is [sic] suspended in 100 ml of water and 10 ml of concentrated hydrochloric acid and treated with a solution of 50 mmol of sodium nitrite in 20 ml of water. After completion of the addition, the mixture is stirred for 4 hours and the product is filtered off.

Alternatively, 30 mmol of compound of the formula 2 are dissolved in 100 ml of ethanol and 50 mmol of alkyl nitrite, preferably pentyl nitrite, are added dropwise. After 4–10 hours, the solvent is removed in vacuo and the crude product is recrystallized from a suitable solvent, preferably alcohol.

TABLE 2

3,6-Dihydropyrazolo[3,4-][1,2,3]triazin-4-ones, Exampes 1–12

| Compound | X | Y | Yield in (%) [sic] | M.p. (° C.) | Recrystallization from: |
|---|---|---|---|---|---|
| 1 | H | 2-F | 66 | 181–185 | EtOH |
| 2 | H | 2-Cl | 84 | 188–190 | EtOH/water |
| 3 | H | 2-CF3 | 42 | 176–179 | EtOH |
| 4 | H | 2-CH3 | 20 | 194–196 | MeOH |
| 5 | H | 3-Cl | 28 | 193–194 | EtOH/water |
| 6 | H | 3-CF3 | 25 | 193–195 | MeOH |
| 7 | H | 4-F | 20 | 192–194 | EtOH |
| 8 | H | 4-Cl | 21 | 195–196 | EtOH |
| 9 | H | 2-Cl-6-F | 59 | 200–203 | EtOH |
| 10 | Me | 2-Cl | 70 | 188–190 | EtOH |
| 11 | Me | 2-Cl-6-F | 79 | 190–192 | EtOH |
| 12 | H | H | 54 | 185–187 | EtOH |

We claim:

1. A compound of Formula 1

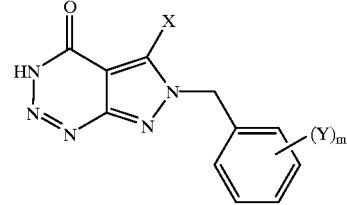

(1)

or their tautomers, in which

X is hydrogen or $C_{1-4}$-alkyl;

Y is hydrogen, halogen, $C_{1-4}$-alkyl, $C_{1-4}$-alkoxy, trifluoromethyl or trifluoromethoxy, and m is a cardinal number from 1 to 2.

2. Compounds of Formula 1 of claim 1, the compounds being:

6-(2-fluorobenzyl)-3,6-dihydropyrazolo[3,4-d][1,2,3]triazin-4-one;

6-(2-chlorobenzyl)-3,6-dihydropyrazolo[3,4-d][1,2,3]triazin-4-one;

6-(2-trifluoromethylbenzyl)-3,6-dihydropyr,3]triazin-4-one;

6-(2-chloro-4-fluorobenzyl)-5-methyl-3,6-dihydropyrazolo[3,4-d][1,2,3]triazin-4-one; or 6-benzyl-3,6-dihydropyrazolo[3,4-d][1,2,3]triazin-4-one.

3. A process for the preparation of 3,6-dihydropyrazolo[3,4-d][1,2,3]triazin-4-ones of Formula (1) of claim 1, which comprises cyclizing with sodium nitrate in an acidic medium a compound of Formula (2)

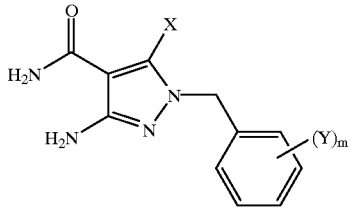

(2)

wherein

X is hydrogen or $C_{1-4}$-alkyl;

Y is hydrogen, halogen, $C_{1-4}$-alkyl, $C_{1-4}$-alkoxy, trifluoromethyl or trifluoromethoxy, and m is a cardinal number from 1 to 2.

4. The process of claim 3, wherein a 3-aminopyrazole-4-carboxamide of Formula (2) is cyclized with an alkyl nitrite in an ethanolic hydrochloric acid.

5. A pharmaceutical composition containing as active substance at least one compound of Formula 1 of claim 1, together with one or more of at least one pharmaceutically acceptable excipient and/or vehicle.

6. A pharmaceutical composition containing as active substance at least one compound of claim 2, together with one or more of at least one pharmaceutically acceptable excipient and/or vehicle.

7. A process for treating epilepsy, which comprises administering to a patient in need therefor an antiepileptically effective amount of the compound of claim 1.

8. A process for treating epilepsy, which comprises administering to a patient in need therefor an antiepileptically effective amount of a compound of claim 2.

* * * * *